United States Patent [19]

Burdick et al.

[11] Patent Number: 5,334,499
[45] Date of Patent: Aug. 2, 1994

[54] METHODS OF EXTRACTING, AMPLIFYING AND DETECTING A NUCLEIC ACID FROM WHOLE BLOOD OR PBMC FRACTION

[75] Inventors: Brent A. Burdick; Tobias D. Ekeze, both of Rochester, N.Y.

[73] Assignee: Eastman Kodak Company, Rochester, N.Y.

[21] Appl. No.: 406,222

[22] Filed: Sep. 12, 1989

Related U.S. Application Data

[63] Continuation-in-part of Ser. No. 339,437, Apr. 17, 1989, abandoned.

[51] Int. Cl.⁵ .......................... C12Q 1/68; G01N 1/10
[52] U.S. Cl. ....................................... 435/6; 424/520; 435/803; 436/177; 935/77; 935/78
[58] Field of Search .................. 435/6, 91, 501, 803; 935/77, 78, 6; 424/520; 436/177

[56] References Cited

U.S. PATENT DOCUMENTS

| | | | |
|---|---|---|---|
| 4,515,890 | 5/1985 | Manderino et al. | 435/7 |
| 4,750,982 | 6/1988 | Tomblin et al. | 204/299 |

FOREIGN PATENT DOCUMENTS

| | | |
|---|---|---|
| 145356 | 6/1985 | European Pat. Off. |
| 237362 | 9/1987 | European Pat. Off. |
| 240191 | 11/1987 | European Pat. Off. |
| 245945 | 11/1987 | European Pat. Off. |

OTHER PUBLICATIONS

Analytical Abstracts Online Abstract, Accession No. 47-09-D-00228, Buffone et al, Clin. Chem., vol. 31(1), Jan. 1985, pp. 164–165.
Maniatis et al, *Molecular cloning: A Laboratory Manual* (New York: Cold Spring Harbor Laboratory), 1982, pp. 280–281.
Wrischnik et al, *Nucleic Acids Res.,* 15(2), pp. 529–542, 1987.
Signer et al., *Nucleic Acids Res.,* 16(15), p. 7738 (1988).
Higuchi, *Amplifications,* May, 1989, pp. 1 and 3.
Kogan et al, *N. Eng. J. Med.,* 317(6), pp. 985–990 (9187).
Saiki et al, *Nature,* 324(6093), pp. 163–166 (1986).
Saiki et al, *Bio/Technology,* 3, pp. 1008–1012 (1985).
Bell et al., *Proc. Natl. Acad. Sci. USA,* 78(9), pp. 5759–5783 (1981).

*Primary Examiner*—Amelia Burgess Yarbrough
*Attorney, Agent, or Firm*—J. Lanny Tucker

[57] ABSTRACT

A nucleic acid is rapidly extracted from whole blood or a peripheral blood mononuclear cell (PBMC) fraction thereof. Extraction from the PBMC fraction is accomplished by heating the fraction at or near the boiling point of water for a few minutes and recovering the extracted nucleic acid. This rapid method is particularly useful for extracting DNA for the detection of genetic diseases or infectious agents, such as HIV-I. Whole blood can likewise be heated after it is mixed with a salt solution containing a polysaccharide, such as dextran. The extracted nucleic acid is then recovered from the heated mixture. Nucleic acids extracted in this way are available for amplification using a polymerase chain reaction. Where the presence of a specific gene is to be determined for diagnostic purposes, it can be extracted as described above and subjected to suitable amplification and detection steps.

7 Claims, No Drawings

METHODS OF EXTRACTING, AMPLIFYING AND DETECTING A NUCLEIC ACID FROM WHOLE BLOOD OR PBMC FRACTION

REFERENCE TO RELATED APPLICATION

This application is a continuation-in-part of U.S. Ser. No. 339,437, filed Apr. 17, 1989 by Burdick and Ekeze, now abandoned.

FIELD OF THE INVENTION

The present invention relates to a method for rapidly extracting a nucleic acid, such as DNA, from either whole blood or the peripheral blood mononuclear cell fraction thereof. It also relates to a method for amplifying or detecting the extracted nucleic acid for diagnostic purposes.

BACKGROUND OF THE INVENTION

Within the field of biological diagnostics, research and analytical procedures require the investigation of nucleic acids from biological specimens, such as whole blood or fractions thereof. Such in vitro procedures require as a first step, the isolation of the nucleic acids. For example, relatively pure samples of genomic DNA are required in order to perform tests for genetic diseases, and recombinant technology requires isolation of both the vector DNA and the DNA to be cloned. In the detection of infectious agents, such as bacteria and virally infected cells, DNA diagnostic procedures generally require cell lysis followed by detection the released DNA.

Generally, DNA does not exist as a free molecule in a cell, but instead exists as a complex association of DNA, RNA and proteins. This is a consequence of the role of DNA as the carrier of genetic information, and its involvment with RNA and various proteins in that function.

Because of this complex association of DNA with other materials in a specimen, effective DNA extraction requires that: the DNA be released through disrupted cell walls and membranes, DNA-protein complexes be dissociated by denaturation or proteolysis, and DNA be separated from other macromolecules. Various means are used in the art to accomplish one or more of these results. Cell lysis can be accomplished, for example, by freeze-thawing, ultrasonic means, shearing and other mechanical techniques, or by treatment with enzymes, surfactants or chelating agents. Proteases and other hydrolyzing agents can be used to dissociate DNA from proteins. Residual proteins and other macromolecules can be extracted using various solvents, such as phenol or other alcohols.

Some DNA isolation techniques are described in, for example, E. P. Publications 145,356 (published Jun. 19, 1985), 240,191 (published Oct. 7, 1987), and 245,945 (published Nov. 19, 1987), all of which use an alcohol and an enzymatic protein decomposer in certain sequences of steps. Generally, these procedures are directed to the extraction of vital DNA and involve a number of complicated steps which must be carried out with precision in order to obtain all available DNA. Thus, many of the known processes are labor intensive, require the use of undesirable solvents and are not readily automated.

Isolation or extraction of the nucleic acid of interest is necessary to take advantage of recent developments for amplification and detection of nucleic acids using polymerase chain reactions. U.S. Pat. Nos. 4,683,195 (issued Jul. 28, 1987 to Mullis et al) and 4,683,202 (issued to Mullis the same day) describe useful amplification and detection procedures for nucleic acids found in various biological specimens using a polymerase. Standard nucleic acid extraction techniques are mentioned by reference to Maniatis et al, *Molecular Cloning: A Laboratory Manual* (New York: Cold Spring Harbor Laboratory, 1982), pp. 280–281. This reference is directed to a standard extraction procedure involving the use of a protease to lyse cells and phenol/chloroform extraction, the entire procedure generally taking many hours to perform and involves the use of hazardous organic solvents. It is also used to extract DNA: from hamster ovary cells by Nunberg et al, *Proc. Natl. Acad. Sci. USA*, 75 (11), pp. 5553–5556 (1978), from the buffy coat of whole blood specimens by Saiki et al, *Bio/Technology*, 3, pp. 1008–1012 (1985), and from whole blood by Bell et al, *Proc. Natl. Acad. Sci. USA*, 78(9), pp. 5759–5763 (1981).

For diagnostic testing to be commercially feasible, it also must be economically competitive. This means that every aspect of the procedure must be simple, easy to use and automated to some extent. Extraction of the DNA from a specimen is one aspect that requires careful development in order to obtain maximum amounts of DNA from the specimen as well as economic advantages. Moreover, in situations where a diagnostic result is needed quickly the extraction procedure should be rapid.

Thus, there has been considerable activity in developing improved DNA extraction procedures which avoid the tedious and time-consuming steps noted above and the use of organic solvents. Thus, Kogan et al, *N. Eng. J. Med.*, 317 (16), pp. 985–990 (1987) describe the extraction of DNA to detect genetic disorders by boiling cells which have been removed from whole blood by centrifugation. The extracted DNA is then subjected to amplification.

Similarly, Saiki et al, *Nature*, 324, pp. 163–166 (1986) describe boiling buffered buffy coat (which includes peripheral blood mononuclear cells and granulocytes) of whole blood to amplify $\beta$-globin DNA. Similar work is shown in EP-A-0 237 362 for detection of sickle cell and HLA DNA. In some cases, the cells of the buffy coat are overlaid with mineral oil prior to the heating step.

While these procedures avoid the tedious phenol/chloroform extraction described above, and appear to be rapid (done in a few minutes), they are largely useful only for extraction of DNA present in large quantities in a whole blood sample, such as HLA or $\beta$-globin DNA. Where the DNA of interest is present in very small quantities, such as in the case of the presence of many infectious agents (such as viruses), further improvements in extraction from whole blood, or a buffy coat fraction, are needed for sensitive detection. Moreover, there are many interferents to polymerase activity which also need to be removed from whole blood prior to amplification.

A more recent advance in the art is described in U.S. Ser. No. 178,202 (filed Apr. 6, 1988 by Higuchi) now abandoned, whereby the defects of the tedious phenol/chloroform procedure are avoided, and which allows extraction of DNA for polymerase chain reaction. It involves the use of a composition containing a nonionic lysing detergent and a proteolytic enzyme. One of the principle advantages of this method is the shortening of the time for DNA extraction to less than two hours.

While this improvement is welcome in the art, there is a continuing need to simplify DNA extraction procedures even further, especially where the DNA is present in very small concentrations in the specimen. In particular, there is a need for a rapid and effective method of extracting HIV-I DNA from whole or a peripheral blood mononuclear fraction thereof.

SUMMARY OF THE INVENTION

The problems of known DNA extraction procedures is overcome with a method for the rapid extraction of a nucleic acid from an aqueous sample of peripheral blood mononuclear cells, the method consisting of:

A. subjecting an aqueous sample of peripheral blood mononuclear cells suspected of containing a nucleic acid from an infectious agent or human genome to heat at or near the boiling point of water for from about two to about fifteen minutes to lyse the cells in the sample and release the nucleic acid from the cells, and B. recovering the nucleic acid from the heated sample.

In addition, a method for amplifying a predetermined nucleic acid using a polymerase chain reaction comprises:

A. an extraction procedure consisting of:
  1) subjecting an aqueous sample of peripheral blood mononuclear cells suspected of containing a nucleic acid from an infectious agent or human genome to heat at or near the boiling point of water for from about two to about fifteen minutes to lyse the cells in the sample and release the nucleic acid from the cells, and
  2) recovering the nucleic acid from the heated sample, and B. amplifying the recovered nucleic acid using a polymerase chain reaction.

Still further, this invention provides a method for the detection of a nucleic acid having two complementary strands, the method comprising:

A. an extraction procedure consisting of:
  1) subjecting an aqueous sample of peripheral blood mononuclear cells suspected of containing a nucleic acid from an infectious agent or human genome to heat at or near the boiling point of water for from about two to about fifteen minutes to lyse the cells in the sample and release the nucleic acid from the cells, and to denature the nucleic acid, and
  2) recovering the denatured nucleic acid from the heated sample, B. contacting the recovered denatured nucleic acid with first and second primers which are complementary to the separated strands of the nucleic acid so as to form hybridized products of the primers and the complementary strands, C. forming first and second extension products of the primers in the hybridized products, which extension products, when separated from their complements, can serve as templates for synthesis of extension products of the primers, D. separating the primer extension products from the templates on which they were synthesized, E. contacting the separated extension products and the predetermined nucleic acid with additional first and second primers, resulting in amplification of the nucleic acid to form complementary products, F. separating the primer extension products from the complementary products formed in step E, and G. detecting the amplified nucleic acid as an indication of the presence of the nucleic acid in the aqueous sample.

Also, a method for the rapid extraction of a nucleic acid from a specimen of whole blood consists of:

A. mixing a whole blood specimen with a salt solution comprising one or more polysaccharides, B. subjecting the mixture resulting from step A to heat at a temperature at least at or near the boiling point of water for from about two to about fifteen minutes to lyse the cells in the mixture and release a nucleic acid from the cells, and C. recovering the nucleic acid from the heated mixture.

The extraction method of this invention is rapid and effective to extract DNA from whole blood or particularly the peripheral blood mononuclear cell fraction (PBMC) fraction obtained therefrom. This method can be carried out in a few minutes, and avoids the tedious, complicated and costly procedures known in the art. Moreover, undesirable organic solvents are avoided, and the procedure is susceptible to automation, for example, in a contained vessel of some type. The use of expensive lysis enymzes, such as proteinase K, is also avoided. It is also evident that the practice of this invention allows one to obtain a nucleic acid even if it is present in very small quantities, as is likely with infectious diseases such as AIDS or other viral infections.

These advantages are achieved solely by heating the PBMC fraction at or near the boiling point of water for at least about two minutes and generally up to about fifteen minutes. This simple step accomplishes the desired result of extracting the DNA from the cellular material most likely to contain it, breaking down DNA-protein complexes, and can also denature the complementary strands of DNA for later amplification or detection. Extracted DNA can be separated from the specimen using suitable techniques. Hemoglobin (a potential interferent for amplification) and other whole blood components incompatible with amplification reagents are avoided by this method.

This invention also provides a means of extracting DNA from whole blood where it is likely that the DNA is present in quantities which will be detectable even after boiling and removal of hemoglobin and other unwanted whole blood components. The whole blood specimen is mixed with a diluent composition comprising a salt and polysaccharide prior to the boiling step. Each of these procedures is described in more detail below.

DETAILED DESCRIPTION OF THE INVENTION

The present invention is directed to the extraction, amplification or detection of one or more predetermined (that is, targeted) nucleic acids from either whole blood or the peripheral blood mononuclear cell fraction (PBMC) thereof. While the primary purpose of the invention is diagnostic, extracted DNA can also be used in various research and medical studies, for cloning DNA or messenger RNA or for sequencing genomic DNA. Other uses for extracted DNA would be readily apparent to one skilled in the art.

DNA can be extracted from human or animal blood, and can be genomic DNA or that generated in cells or body fluids by infectious agents such as bacteria, viruses or yeasts. Where the specimen treated is whole blood, generally the nucleic acid extracted is genomic DNA. However, this invention is particularly useful for extracting and detecting DNA from cells invaded by infectious agents (most likely viruses such as herpes, Cytomegalovirus, Epstein-Barr virus, hepatitis, rubella, and retroviruses such as HIV-I, HIV-II and HTLV-I). Preferably, Cytomegalovirus, Epstein-Barr viral and HIV-I viral DNA are extracted and detected with the present invention, with the extraction and detection of HIV-I viral DNA being most preferred.

In a preferred embodiment, the extracted nucleic acid is amplified or detected using polymerase chain reaction (described in more detail below).

The peripheral blood mononuclear cell fraction (PBMC) is obtained from whole blood by centrifugation onto a cushion of Ficoll-Paque TM (Pharmacia Inc., Piscataway, N.J.), using standard procedures. It is believed to be composed of monocytes and lymphocytes.

When working with PBMC, the critical step in the extraction method of this invention is to subject an aqueous sample of the cells to heat at or near the boiling point of water for a sufficient time to break down proteins and lyse all cells in the sample. The sample may contain a buffer as the medium, but in some instances the medium is merely water. The temperature for this step would vary depending upon atmospheric pressure, the time of boiling and other environmental factors. Generally, at sea level, the temperature for heating would be at or near 100° C., but could be as low as 80° C. and as high as 120° C.

The time of maintaining the sample at the temperature noted above is that needed to denature the proteins and lyse the cells in the sample to release DNA. This can be readily determined by taking portions of the sample during the heating step and determining whether whole proteins remain. The time will also vary with the temperature used, that is, the lower the temperature, the longer the period of heating time. Generally, the sample is heated at the desired temperature for at least about two minutes and up to about fifteen minutes, and preferably from about four to about twelve minutes, with about ten minutes being optimum.

Heating can be carried out in any suitable vessel which is sufficient in size to hold the sample and which can withstand the heating procedure. For example, it can be carried out in flasks, test tubes, centrifuge tubes, capillary tubes, beakers, cuvettes and other standard laboratory equipment. Preferably, it is carried out in a self-contained reaction vessel which is designed for various procedures including heating and chemical reactions. Many such vessels are known in the art. A preferred self-contained vessel is described in copending U.S. Ser. No. 339,923 (filed Apr. 1, 1989 by Schnipelsky et al), incorporated herein by reference.

After heating to lyse the PBMC in the sample, the released nucleic acid (generally, DNA) is recovered in a suitable manner. Cellular matter and any coagulated debris are separated from the fluid containing soluble DNA molecules in any suitable manner, including filtration, centrifugation, decanting or siphoning. Filtration can be carried out using standard filtration equipment, or various devices having filtration membranes. Particularly useful separation means are microporous filter membranes such as the polyamide membranes marketed by Pall Corp. (for example as Loprodyne TM or Biodyne TM membranes). They can be used uncoated or precoated with surfactants or other materials which facilitate the analytical procedures.

The membranes can be used as a separate substrate with suitable containers for carrying out other steps of the assay. Preferably, however, it is mounted as part of a test device. Various test devices are known in the art including those described in U.S. Pat. Nos. 3,825,410 (issued Jul. 23, 1974 to Bagshawe), 3,888,629 (issued Jun. 10, 1975 to Bagshawe), 3,970,429 (issued Jul. 20, 1976 to Updike) and 4,446,232 (issued May 1, 1984 to Liotta). Particularly useful devices are described in copending U.S. Ser. No. 98,248 (filed Sep. 18, 1987 by Hinckley et al) now abandoned.

In one embodiment of this invention where whole blood is treated to extract a nucleic acid, before heating, the whole blood sample is diluted with a solution of one or more polysaccharides in a dilute aqueous salt solution. The polysaccharide acts as a diluent and may aid in eventual separation of extracted DNA from unwanted cellular debris and hemoglobin. A nonionic surfactant, such as a polyoxyethylene ether, polyoxyethylenesorbitan derivative or polyglycol ether can be included in this solution, if desired, in an amount of up to about 10 weight percent. Other useful surfactants would be readily apparent to one skilled in the art, especially after consulting the standard reference for surfactants, *McCutcheon's Emulsifiers and Detergents*, 1986 North American Edition, McCutcheon Division Publishing Co., Glen Rock, N.J. Particularly useful surfactants include Triton TM X-100 and others commercially available such as Nonidet NP-40 and Brij 35 (both trademarks).

The amount of polysaccharide can be varied but it is generally used in an amount to provide from about 1 to about 10 weight percent based on the whole blood sample. From about 3 to about 5 weight percent is preferred.

Useful polysaccharides are generally water-soluble or -dispersible carbohydrates containing at least three simple sugar molecules. They include, but are not limited to, cellulose and cellulosic derivatives, carboxymethylated polysaccharides, lipopolysaccharides, dextrans, dextrins and starches. Particularly useful materials are known as dextrans which have a backbone of D-glucose units linked predominantly $\alpha$-D(1–6) and a molecular weight of at least about 1000. Representative dextrans are described by Jeanes et al, J. A. C. S., 75, pp. 5041–5052 (1954) and Bankert et al, *J. Immun.*, 123 (6), PP. 2466–2474 (1979). Many dextrans are commercially available.

The salt solution includes one or more simple salts, such as sodium chloride, potassium chloride, lithium chloride, magnesium chloride, sodium sulfate, sodium citrate and others which would not interfere with the extraction and isolation of DNA from the cells in whole blood. Basically, the salt solution serves to dissolve the polysaccharide and provide an isotonic solution. The amount of salt in the solution is generally from about 0.5 to about 1.5 weight percent.

The aqueous salt solution can also contain a buffer that is compatible with the biological specimen. Useful buffers include, but are not limited to, phosphate, borate, tris(hydroxymethyl)aminomethane, N-tris(hydroxymethyl)methylaminoethanesulfonic acid and others known in the art.

Contact of the whole blood sample with one or more buffer solutions before the heating step of this invention is not essential, but is desirable in some instances. A useful buffer solution is identified herein as the "TE" buffer, the composition of which is shown below. The TE buffer is generally used to dissolve nucleic acids, particularly DNA. It contains ethylenediaminetetraacetic acid to chelate any heavy metal ions.

As used herein in referring to primers, probes or nucleic acid fragments to be detected, the term "oligonucleotide" refers to a molecule comprised of two or more deoxyribonucleotides or ribonucleotides, and preferably more than three. The exact size is not critical but depends upon many factors including the ultimate use or function of the oligonucleotide. The oligonucleotide may be derived synthetically or by cloning.

The term "primer" refers to an oligonucleotide, whether naturally occurring or synthetically produced, which is capable of acting as a point of initiation of synthesis when placed under conditions in which synthesis of a primer extension product complementary to a nucleic acid strand is induced. Such conditions include the presence of nucleotides (such as the four standard deoxyribonucleoside triphosphates) and an agent for polymerization such as a DNA polymerase, and suitable temperature and pH.

In the practice of this invention, primers, probes and fragments are substantially complementary to a specific nucleic acid sequence of the targeted nucleic acid extracted from whole blood or PBMC fraction. By "substantially complementary" is meant that there are a sufficient number of bases on complementary materials that match so that hybridization will occur. It does not mean, however, that every base pair will match.

In the amplification and detection methods of this invention, useful primers can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use. Naturally occurring primers isolated from biological sources are also useful (such as restriction endonuclease digests).

In some embodiments, at least one of the primers (or sets thereof) used in the detection method is labeled with a specific binding ligand. The term "labeled" refers to the fact that the ligand is attached to this primer in a manner such that it will not readily be detached. The specific binding ligand can be biotin or a derivative thereof, avidin, streptavidin or a derivative thereof, a lectin, a sugar, a protein, a hapten, a drug, or an immuno-logical species, such as an antibody or an antigenic material. Further details about such primers and their use are provided in copending U.S. Ser. No. 273,779 (filed Nov. 21, 1988 by Burdick et al) now abandoned, incorporated herein by reference.

The present invention is useful for amplification or detection of a targeted nucleic acid having two complementary strands. Most nucleic acid sequences of interest already are double-stranded, such as those found in DNA. However, single-stranded nucleic acid sequences, such as mRNA, can be similarly amplified and detected.

A specific nucleic acid sequence is produced using the nucleic acid containing that sequence as a template. If the nucleic acid contains two strands, it is necessary to separate the strands (called denaturation), either as a separate step or simultaneously with the formation of primer extension products. Denaturing can be accomplished using any suitable physical, chemical or enzymatic means as described in the art. Heating to a suitable temperature is a preferred means. Denaturing can occur when the whole blood or PBMC sample is heated to extract DNA.

Once the separated strands are available for use, synthesis of additional nucleic acid strands can be carried out using two or more primers (labeled or unlabeled) in a buffered aqueous solution generally at a pH of from about 7 to about 9. Preferably, a molar excess of the two primers is added to the buffered solution, and specific amounts are taught in the art (for example, U.S. Pat. No. 4,683,202, noted above). The deoxyribonucleoside triphosphates dATP, dCTP, dGTP and dTTP are also added to the synthesis mixture in adequate amounts and the resulting solution is heated to about 90°–100° C. for up to 10 minutes, and preferably from about 1 to about 4 minutes. Enzyme cofactors, such as magnesium or manganese ions, are also preferably present in molar excess to the triphosphates. After this heating, the solution is preferably cooled to room temperature, and an appropriate agent for inducing (or catalyzing) the formation of primer extension products is introduced. This inducing agent is generally known in the art as a polymerization agent. Reaction to form these products is carried out under known conditions (generally from room temperature to that temperature at which polymerization no longer occurs).

The polymerization agent may be any compound, or combination of reagents, which will function to accomplish the synthesis of primer extension products, including enzymes (for example, *E. coli* DNA polymerase I, T4 DNA polymerase, Klenow polymerase, reverse transcriptase and others known in the art). Particularly useful enzymes are thermally stable enzymes, cloned or naturally occurring, such as those obtained from various Thermus bacterial species. Other polymerization agents are described in U.S. Pat. No. 4,683,202 (noted above), incorporated herein by reference.

Preferred thermal-stable enzymes are DNA polymerases from *Thermus aquaticus* as described in E. P. Publication 258,017 (published Mar. 2, 1988). Those polymerases generally have a molecular weight of about 86,000–90,000 daltons. Other useful enzymes are described by Rossi et al, *Syst. Appl. Microbiol.* 7(2–3), pp. 337–341, 1986. Some useful polymerases are commercially available. Generally, the synthesis of extension products will be initiated at the 3' end of each primer and proceed in the 5' to 3' direction along the template until synthesis is terminated. Some polymerization agents (for example, reverse transcriptase) may proceed in the 3' to 5' direction along the template.

The newly formed primer extension products comprising the newly synthesized strands and their respective primers form double-stranded molecules with the initial target strands which are used in the succeeding steps of the method. These strands are then separated by denaturation as described above to provide single-stranded molecules, onto which new nucleic acids are synthesized as described above. Additional reagents may be needed to keep the amplification procedure going, after which most of the extension products will consist of the specific nucleic acid sequence bounded by the two primers (that is, complementary products).

The steps of strand separation and extension product synthesis can be repeated as often as needed to produce the desired quantity of the specific nucleic acid needed for the use, for example detection. Generally, the sequence of steps is repeated at least once, and preferably at least 10 to 50 times.

When it is desired to produce more than one targeted extracted nucleic acid, the appropriate number of sets of primers are used in the general procedure described above.

Various detection procedures can be used to determine the presence of the detectable hybrid including Southern blot, gel electrophoresis, staining and others known in the art.

At any point in the method of this invention after the generation of at least one primer extension product, that product can be hybridized with a detectably labeled probe (described below).

Generally, once a desired amount of the nucleic acid sequence of interest has been generated and the primer extension products are separated for a last time, the first primer extension product is contacted with an oligonucleotide probe which is labeled for detection and is complementary thereto to form a product. The probe comprises an oligonucleotide which is complementary with the targeted nucleic acid sequence. The probes can be of any suitable length of nucleic acids, but preferably they have from about 15 to about 40 nucleic acids. They are labeled (commonly at the 5' end) with any suitable detectable material which will not interfere with the complexation of the specific binding ligand and its receptor. Procedures for attaching labels and preparing probes is well known in the art, for example, as described by Agrawal et al, *Nucleic. Acid Res.*, 14, pp. 6227–45 (1986), and in the references noted above for attaching a specific binding ligand to a primer. Useful labels include radioisotopes, electron-dense reagents, chromogens, fluorogens, phosphorescent moieties, ferritin and other magnetic particles, chemiluminescent moieties and enzymes (which are preferred). Useful enzymes include, glucose oxidase, peroxidase, uricase, alkaline phosphatase and others known in the art. Substrates and dye forming compositions for such enzymes are well known.

In a particularly preferred embodiment, the label is peroxidase, and at some point in the assay, hydrogen peroxide and suitable dye-forming compositions are added to provide a detectable dye. For example, useful dye-providing reagents include tetramethylbenzidine and derivatives thereof, and leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide. Particularly useful dye-providing compositions are described in WO-A-O 88/02806 and 88/02807 (both filed Aug. 16, 1988) and U.S. Ser. No. 136,166 (filed Dec. 18, 1987 by McClune et al) U.S. Pat. No. 5,024,935.

Detection of the presence of the probe which is in the complementary product can be achieved using suitable and known detection equipment and procedures. Certain probes may be visible to the eye without the use of detection equipment.

In order for the probe in the complementary product to be detected, it is often important for the complementary product to be separated from the other materials in the reaction medium. This can be done by suitable insolubilization means, such as by using a primer or probe which is attached or capable of becoming attached to a solid material at some point in the method. The resulting insolubilized complexed product can be separated from uncomplexed materials by filtration, centrifugation or other suitable separation techniques.

Particularly useful separation means are microporous filter membranes such as the polyamide membranes marketed by Pall Corp. (described above). The membranes can be used as a separate substrate with suitable containers for carrying out other steps of the assay. Preferably, however, they are mounted as part of a test device, as described above.

The method described herein can be used to provide the detection or characterization of specific nucleic acid sequences associated with infectious diseases, genetic disorders or cellular disorders such as cancers found in biological specimens. It may also be used in forensic investigations, DNA typing and tissue typing. For purposes of this invention, genetic diseases include specific deletions or mutations in human genomic DNA from any organism, such as sickle cell anemia, cystic fibrosis, α-thalassemia, β-thalessemia and others readily apparent to one skilled in the art. Various infectious diseases can be diagnosed by the presence cells of small quantities of specific DNA sequences characteristic of the organism, whether it be a yeast, bacterium or virus. Such bacteria which can be detected include, but are not limited to, Salmonella, Chlamydia, Gonorrhea, Shigella and Listeria. Viruses which are detectable include, but are not limited to, herpes, Cytomegalovirus, Epstein-Barr virus, hepatitis and retroviruses such as HTLV-I and HIV--I. Protozoan parasites, yeasts and molds are also detectable. Other detectable species would be readily apparent to one skilled in the art.

The method of the present invention can also be used to screen neonates for the presence of HIV-I. Whole blood from neonates is withdrawn, spotted onto filter paper or another suitable porous substrate and dried. The portion of the substrate having the dried blood sample is then cut out and put into a solution containing dextran (or other suitable polysaccharide, 3 weight %), Triton TM X-100 (or other suitable nonionic surfactant, 10 weight %) and sodium chloride (or other suitable salt, 0.9 weight %) in water (250 μl ). This mixture is then heated at about 118° C. for about 5 minutes to extract DNA. The extracted DNA can then be amplified using polymerase chain reaction and detected as described herein.

The following examples are included to illustrate the practice of this invention, and are not meant to be limiting in any way.

The materials used in these examples were as follows:

The "TE" buffer was composed of tris(hydroxymethyl)aminomethane hydrochloride buffer (10 mmolar), and ethylenediaminetetraacetic acid (1 mmolar), and the pH was adjusted to 8 using hydrochloric acid.

The "running buffer" (pH 8) used for electrophoresis was composed of tris(hydroxymethyl)aminomethane (89 mmolar), boric acid (89 mmolar) and ethylenediaminetetraacetic acid (2 mmolar).

Hanks balanced salt solution was obtained from Sigma Chemical Co.

Example 1

Extraction Of HIV-I DNA from PBMC Fraction of Whole Blood

This example illustrates how a nucleic acid can be extracted from a PBMC fraction of whole blood. It shows the standard method for obtaining the PBMC fraction, and then demonstrates the extraction, amplification and detection procedures of this invention.

Peripheral blood mononuclear cells (PBMC) were obtained from whole blood samples of patients suspected of carrying HIV-I using the following procedure:

Whole blood (10 ml), collected in heparin tubes, was added to 15 ml centrifuge tubes and centrifuged at 1200 rpm for 10 minutes. All layers were removed and saved except about 0.5 ml of the plasma layer. Leaving behind as much as possible of the red blood cells, as much as possible of the buffy coat was removed and transferred to a 15 ml centrifuge tube. Hanks balanced salt solution (HBSS, 5 ml) was then added to the buffer coat cells, which were then underlayered with Ficoll-Paque ™ (3.5 μl). The resulting mixture was centrifuged at 1900 rpm for 16 minutes, then the band of PBMC above the ficoll layer was removed and transferred to another 15 ml centrifuge tube. HBSS (5 ml) was added and the mixture was centrifuged at 1200 rpm for 10 minutes. The resulting pellet containing the equivalent of 250–300 μl of PBMC was transferred to a 2 ml screw-cap microtube and stored at −70° C.

A sample (1 ml) of PBMC containing about 2–3 million cells/ml was placed into a 1.5 ml Eppendorf microcentrifuge tube and centrifuged at 14,000 rpm for 10 minutes. The supernatant was discarded and the pellet was resuspended in "TE" buffer (1 ml). The sample was heated at 100° C. for 10 minutes, then centrifuged at 14,000 rpm for 2 seconds. Samples (50 μl) of the supernatant were mixed with 100 μl of the following polymerase chain reaction mixture. Amplification was carried out as described below.

The polymerase chain reaction mixture contained the following: tris(hydroxymethyl)aminomethane hydrochloride buffer (pH 8, 10 mmolar), potassium chloride (50 mmolar), magnesium chloride (10 mmolar), gelatin (100 μg/ml), deoxyribonucleoside triphosphates (dNTPs, 0.17 mmolar each) and DNA polymerase isolated from *Thermus aquaticus* (7.5 units). The primers used (1 μmolar of each) had the following nucleotide sequences:

5'-ATAATCCACCTATCCCAGTAG-
GAGAAAT-3'

5'-X-TTTGGTCCTTGTCTTATGT-
CCAGAATGC-3' wherein X represents a biotintetraethylene glycol spacer arm prepared and attached to the nucleic acid sequence as described in U.S. Ser. No. 104,200 (filed Oct. 2, 1987 by Levenson et al).

The reaction mixture and the PBMC fractions were mixed and amplified by polymerase chain reaction for 35 cycles, repeating the cycle: 97° C. for 0.5 minute (denaturing), 55° C. for 0.5 minute (hybridize) and 70° C. for 1 minute (primer extension product formation).

Aliquots (6 μl) were withdrawn and applied to 4% agarose gel (3% NuSieve ™ and 1% Seakem ™) from FMA BioProducts (Rockland, Mass.). The gel was prestained with 4 μl of an ethidium bromide solution (10 mg/ml) in water (Sigma Chemical Co.). The running buffer (600 μl) contained 24 μl ethidium bromide. The gel was electrophoresed at 120 volts for 1 hour, then photographed and the bands were visualized. The results showed strong bands indicating isolation and amplification of the HIV-I DNA from the PBMC fraction. No bands were seen from the Control solution known to contain no HIV-I DNA.

Example 2

Extraction and Detection of Human β-Globin DNA from Whole Blood

This example illustrates the extraction and detection of Human β-globin DNA from whole blood that was obtained from patients, then spotted on filter paper and dried.

Whole blood samples (50 μl) were obtained from neonates and spotted onto standard filter paper and air dried at room temperature for 4 hours. The circular spots of dried blood were cut out with the paper substrate still attached, and added to a solution of dextran (3 weight %) and Triton ™ X-100 (10 weight %) in a sodium chloride (0.9 weight %) solution (250 μl). The resulting mixture was vortexed for 10 seconds, then heated at 118° C. for 5 minutes. The heated mixture was filtered through a 0.45 μm filter and the filtrate (10–20 μl portions) was used for polymerase chain reaction amplification procedures.

The polymerase chain reaction mixture contained the following: potassium chloride (0.05 molar), magnesium chloride (2.5 mmolar), gelatin (100 μg/ml), tris(hydroxymethyl)aminomethane hydrochloride (pH 8, 0.01 molar), deoxyribonucleoside triphosphates (dNTPs, 0.175 mmolar each) and DNA polymerase isolated from *Thermus aquaticus* (8 units). The primers (0.2 μmolar each) had the nucleotide sequences as follows:

5'-ACACAACTGTGTTCACTAGC-3'

5'-CAACTTCATCCACGTTCACC-3'

The reaction mixture (94 μl) was mixed with the extracted whole blood solution (10–20 μl) and amplification was carried out for 30 cycles, repeating the cycle: 95° C. for 0.5 minute (denaturing), 55° C. for 0.5 minute (hybridization) and 70° C. for 1 minute (primer extension product formation).

Aliquots (5 μl) were withdrawn and assayed using gel electrophoresis and ethidium bromide staining. The results showed strong bands for the tests, indicating successful isolation and amplification of DNA obtained from the neonate samples. A negative control sample known to contain no Human β-globin DNA showed no bands.

EXAMPLE 3

Extraction and Detection of Human Leukocyte Antigen DNA from Whole Blood

This invention demonstrates the extraction of Human Leukocyte Antigen DNA from whole blood using the method of this invention.

Whole blood samples (100 μl) from patients were placed in 1.5 ml Eppendorf tubes, and a solution (250 μl) containing dextran (3 weight %) and sodium chloride (0.9 weight %) was added, followed by thorough mixing by inverting the tubes. The tubes were then heated in boiling water for 5 minutes, then centrifuged for 10 seconds. The supernatant was removed and placed in clean 1.5 ml Eppendorf tubes. Aliquots were removed, mixed with the polymerase chain reaction mixture described below, and amplified as described below.

The polymerase chain reaction mixture contained potassium chloride (0.05 molar), magnesium chloride (2.5 mmolar), gelatin (100 μg/ml), tris(hydroxymethyl)aminomethane buffer (pH 8, 0.01 molar), deoxyribonucleoside triphosphates (dNTPs, 0.175 mmolar each), DNA polymerase isolated from Thermus aquaticus (8 units). The primers (24 μl, 10 μmolar each) had the following nucleotide sequences:

5'-GTGCTGCAGGTGTAAACTTGTACCAG-3'

5'-CACGGATCCGGTAGCAGCG-GTAGAGTTG-3'

The reaction mixture (94 μl) was mixed with the extracted whole blood solution (10 μl) and the amplification reaction was carried out for 30 cycles, repeating the following cycle: 90° C. for 0.5 minute (denaturing), 55° C. for 0.5 minute (hybridization) and 70° C. for 1 minute (primer extension product formation).

Aliquots (5 μl) were withdrawn and assayed using gel electrophoresis and ethidium bromide staining. The results showed strong bands for the sample indicating successful extraction and amplification of Human Leukocyte Antigen DNA from the samples. A control known to contain no such DNA showed no bands.

The invention has been described in detail with particular reference to preferred embodiments thereof, but it will be understood that variations and modifications can be effected within the spirit and scope of the invention.

We claim:

1. A method for the rapid extraction of a nucleic acid from a specimen of whole blood, said method consisting of:
   A. mixing a whole blood specimen with a salt solution comprising one or more polysaccharides,
   B. subjecting the mixture resulting from step A to heat at a temperature at least at or near the boiling point of water for from about two to about fifteen minutes to lyse the cells in said mixture to release a nucleic acid from said cells, and
   C. recovering said nucleic acid from said heated mixture.

2. The method of claim 1 wherein said polysaccharide is a dextran present in an amount of from about 1 to about 10 weight percent of said whole blood specimen.

3. The method of claim 1 wherein said salt solution further comprises a nonionic surfactant.

4. The method of claim 1 for the extraction of either Human β-globin or Human Leukocyte Antigen DNA.

5. The method of claim 1 wherein said mixture is heated for from about four to about twelve minutes at a temperature of from about 95° to about 120° C.

6. The method of claim 2 wherein said nucleic acid is extracted from a dried whole blood specimen.

7. The method of claim 1 for the extraction of a nucleic acid from cells which have been infected by an agent selected from the group consisting of herpes, hepatitis, rubella, Epstein Barr virus, cytomegalovirus and a retrovirus.

* * * * *